United States Patent [19]
Hohenstein et al.

[11] Patent Number: 5,775,342
[45] Date of Patent: Jul. 7, 1998

[54] HAIR WAVING METHOD USING ACIDIC REDUCING SOLUTION CONTAINING ALCOHOL AMINE SULFITE

[75] Inventors: Karen Hohenstein, Culver City; George Andrassy, Walnut, both of Calif.

[73] Assignee: Dep Corporation, Rancho Dominguez, Calif.

[21] Appl. No.: 644,528

[22] Filed: May 10, 1996

[51] Int. Cl.$^6$ .................................................. A45D 7/04
[52] U.S. Cl. ....................................................... 132/204
[58] Field of Search ................................. 132/202, 203, 132/204, 205; 424/70.2, 70.5

[56] References Cited

U.S. PATENT DOCUMENTS

| | | | |
|---|---|---|---|
| 2,437,965 | 3/1948 | Michaels et al. | 132/204 |
| 2,651,718 | 6/1953 | Speakman | 132/204 |
| 2,840,086 | 6/1958 | Whitman et al. | 132/204 |
| 3,063,908 | 11/1962 | Kalopissis | 132/204 |
| 3,567,363 | 3/1971 | Wolfram . | |
| 4,011,878 | 3/1977 | Abegg et al. | 132/204 |
| 4,313,933 | 2/1982 | Yamazaki | 132/204 |
| 5,533,532 | 7/1996 | Hawkins et al. | 132/204 |

FOREIGN PATENT DOCUMENTS 2090303   7/1982   United Kingdom ................. 132/204

*Primary Examiner*—Todd E. Manahan
*Attorney, Agent, or Firm*—Blakely, Sokoloff, Taylor & Zafman, LLP

[57] ABSTRACT

A process and composition for waving or straightening hair by treating the hair with an acidic reducing solution containing an amine sulfite, having a pH in the range of 5.0 to 6.95, followed by applying an alkaline oxidizing solution containing hydrogen peroxide, and having a pH in the range of 7.50 to 10.0 The process and composition solves certain problems which are commonly encountered in waving or straightening products, such as loss of hair color, and hair damage.

12 Claims, No Drawings

HAIR WAVING METHOD USING ACIDIC REDUCING SOLUTION CONTAINING ALCOHOL AMINE SULFITE

BACKGROUND OF THE INVENTION

1. Field of the Invention

The present invention relates generally to compositions and processes for waving or straightening hair, and more particularly to a composition and a process which utilizes an acidic reducing solution and an alkaline oxidizing solution.

2. Description of Related Art

Neutral or alkaline sulfites or bisulfites have been used to wave or straighten hair, as disclosed in U.S. Pat. Nos. 4,296,764; 3,864,476; and 2,836,185. These compositions are relatively unreactive in alkaline and neutral environments. The result of using these compositions are slow processing time following the application of these chemicals to the hair, slow diffusion of the compositions into the cortex of the hair, and low cleavage rates of the disulfide bonds, all of which yield a poor quality curl. Sometimes, a swelling agent such as urea, is added to the compositions to improve the reaction rate. However, these agents often cause loss of natural hair color, hair damage, and an unpleasant sensation of a residue on the hair, after processing is completed.

Therefore, it is desirable to provide a composition and process for waving and straightening hair which has a quicker reaction time, and leaves the hair in good condition, with little loss of natural color and no unpleasant residue.

Further, prior known processes used an acidic solution of hydrogen peroxide to neutralize the hair during the treatment process. Acidic hydrogen peroxide neutralizers will oxidize the sulfhydryl groups formed in the waving process to disulfide bonds. However, the acidic solution has little impact on the Bunte salts that are also formed in the reaction, and leave the hair with a rough feel, and result in poor curl formation and hair damage.

BRIEF DESCRIPTION OF THE INVENTION

This invention involves a process for waving or straightening hair comprising treating the hair with an acidic reducing solution consisting of an aqueous solution of amine sulfite. Unlike the sodium and ammonium (bi)sulfites previously used, the amine sulfite, of the present invention, is easily buffered to form stable acidic solutions. Further, the composition penetrates the cortex of the hair without the need of harsh swelling agents.

The hair is then treated with an alkaline oxidizing solution that consists of a mixture of an acidic solution containing hydrogen peroxide, and an alkaline solution of alkanolamine or alkali metal hydroxides or ammonium hydroxide. The resulting alkaline oxidizing solution neutralizes both the sulfhydryl groups and the Bunte salts formed by the acidic reducing solution, to disulfide bonds. This reaction leads to good curl formation, and leaves the hair in good condition.

DETAILED DESCRIPTION

An acidic reducing solution for hair waving or straightening for use in this invention comprises an aqueous solution of amine sulfite, preferably ethanolamine sulfite, having a pH between 5.50 to 6.95. The reducing agent, the amine sulfite, is present in an amount ranging from 5 to 35% by weight relative to the total weight of the reducing solution.

The preferred composition of the reducing solution has a pH range of 6.1 to 6.5; and the reducing agent is ethanolamine sulfite, 60% solution, and is present in an amount ranging from 10 to 25% by weight relative to the total weight of the solution. The same formulation is suitable for waving or straightening hair.

The preferred composition of the acidic reducing solution is as follows:

| Ingredients | Amount, % by weight |
| --- | --- |
| Glycerin or propylene glycol | 5.0 to 10.0 |
| Polysorbate 20 | 2.0 |
| Ethanolamine sulfite, 60% | 25.0 |
| Citric acid | 3.2, q.s. to pH 6.1 to 6.50 |
| Fragrance oil | 0.5 |
| Water | q.s. to 100 |

An alkaline oxidizing solution for use in this invention comprises two solutions, an acidic solution containing hydrogen peroxide, and an alkaline solution of alkanolamine or alkali metal hydroxides or ammonium hydroxide. Although the compositions of the acidic solution and the alkaline solution may vary, the desired formulations combine to form an alkaline oxidizing solution having a pH in the range of 7.50 to 10.0, and containing hydrogen peroxide in the amount of 0.5 to 5.00% by weight. The preferred alkaline oxidizing solution has a pH in the range of 8.50 to 9.50 and contains hydrogen peroxide in the amount of 1.80 to 2.20% by weight. The alkaline oxidizing solution is mixed immediately before application, in a ratio of 100 grams of the acidic solution to 18 grams of the alkaline solution.

More specifically, the ingredients of the preferred acidic solution may be expressed as follows:

| Ingredients | Amount, % by weight |
| --- | --- |
| Phosphoric acid, 85% | 0.01 |
| Monosodium phosphate | 0.42 |
| Hydrogen peroxide, 25% | 8.4 |
| Nonoxynol-10 | 1.0 |
| Fragrance oil | 0.5 |
| Water | q.s. to 100 |

The alkaline solution may comprise an aqueous solution of sodium or potassium hydroxide. The preferred alkaline solution comprises an aqueous solution of triethanolamine, having a concentration of 12% by weight of triethanolamine.

In practice, this invention may be executed by use of the following procedures, which are the preferred steps of this invention.

When waving hair is desired, the hair is first wet thoroughly, then towel-dried. The hair is wound onto permanent wave rods, curlers, or other devices used in waving hair. The acidic reducing solution is applied to the hair and allowed to process for fifteen to ninety minutes, depending on the hair type and the degree of curl desired. The processing time may be shortened by wrapping the wound hair with plastic wrap or some other type of covering to prevent evaporation of the reducing solution, and applying heat, such as with a hairdryer. At the end of the processing time, the hair is rinsed thoroughly with water and blotted with a towel to absorb excess moisture. The alkaline oxidizing solution is mixed, applied to the hair and allowed to process for five to ten minutes. The rods are then removed from the hair, the hair is thoroughly rinsed, towel-dried, and styled as desired.

When the straightening hair is desired, the hair is first wet thoroughly, then towel-dried. The acidic reducing solution is applied to the hair and gently combed through the hair. The hair is allowed to process for fifteen to ninety minutes, depending on the degree of straightness desired. The hair is then rinsed and gently blotted with a towel to remove excess moisture. The alkaline oxidizing solution is mixed and applied to the hair. The mixture is gently combed through the hair and allowed to process for five to ten minutes. The hair is then rinsed, towel-dried, and styled as desired.

It is appreciated that other modifications and variations of the compositions and procedures, such as the inclusion of conditioners, preservatives, or coloring agents might be made by those skilled in the art without departing from the spirit and scope of the present invention.

What is claimed is:

1. A process for waving or straightening hair, comprising the steps of:
    applying to hair an effective amount of an acidic reducing solution including an alcohol amine sulfite;
    setting the hair in the desired formation;
    rinsing the hair to remove the acidic reducing solution; and
    treating the hair with an alkaline oxidizing solution comprising a mixture of a hydrogen peroxide solution and an alkaline solution.

2. A process as defined in claim 1, wherein the alcohol amine sulfite is ethanolamine sulfite.

3. A process as defined in claim 2, wherein the ethanolamine sulfite is present at a concentration of 5 to 35% by weight, and the acidic reducing composition has a pH between 5.50 to 6.95.

4. A process as defined in claim 3, wherein the acidic reducing composition has a pH between 6.10 to 6.50, and the ethanolamine sulfite is present at a concentration of 10 to 25% by weight.

5. A process as defined in claim 1, wherein the alkaline oxidizing solution is mixed just prior to application of the alkaline oxidizing solution to the hair.

6. A process as defined in claim 1, wherein the alkaline oxidizing solution has a concentration of hydrogen peroxide of 0.50 to 5.00% by weight, and has a pH in the range of 7.50 to 10.0.

7. A process as defined in claim 6, where in the alkaline oxidizing solution has a concentration of hydrogen peroxide of 1.8 to 2.2% by weight, and has a pH in the range of 8.50 to 9.50.

8. A kit for use in hair waving or straightening applications solutions comprising:
    an acidic reducing solution having a pH in the range of 5.50 to 6.95 and said acidic reducing solution containing a reducing agent of amine sulfite; and
    an alkaline oxidizing solution comprising, an acidic hydrogen peroxide solution, and an alkaline solution of alkanolamine, alkali metal hydroxide or ammonium hydroxide, having a pH in the range of 7.50 to 10.0, and containing hydrogen peroxide in an amount of 0.5 to 5.00% by weight.

9. A kit as defined in claim 8, wherein;
    the reducing agent of the acidic reducing solution is ethanolamine sulfite, in the amount of 5 to 35% by weight;
    the acidic reducing solution has a pH in the range of 6.10 to 6.50; and
    the alkaline oxidizing solution has a pH in the range of 8.50 to 9.50, and contains hydrogen peroxide in the amount of 1.8 to 2.20% by weight.

10. A kit as defined in claim 8, wherein;
    the alkaline solution comprises an aqueous solution of triethanolamine, having a concentration of 12% by weight of triethanolamine.

11. A kit as defined in claim 8, wherein;
    the alkaline solution comprises an aqueous solution of sodium hydroxide, having a concentration of 2% by weight of sodium hydroxide.

12. A kit as defined in claim 8, wherein;
    the alkaline solution comprises an aqueous solution of potassium hydroxide, having a concentration of 2% by weight of potassium hydroxide.

* * * * *

UNITED STATES PATENT AND TRADEMARK OFFICE
CERTIFICATE OF CORRECTION

PATENT NO. : 5,775,342
DATED : July 7, 1998
INVENTOR(S) : Hohenstein et al.

It is certified that error appears in the above-identified patent and that said Letters Patent is hereby corrected as shown below:

In column 2, at line 14 (inside table), please delete "oii" and insert --oil--.

Signed and Sealed this

Eighteenth Day of May, 1999

Attest:

Q. TODD DICKINSON

*Attesting Officer*  Acting Commissioner of Patents and Trademarks